US010019060B2

United States Patent
Cash

(10) Patent No.: US 10,019,060 B2
(45) Date of Patent: Jul. 10, 2018

(54) MIND-CONTROLLED VIRTUAL ASSISTANT ON A SMARTPHONE DEVICE

(71) Applicant: Duane Matthew Cash, Mountain View, CA (US)

(72) Inventor: Duane Matthew Cash, Mountain View, CA (US)

( * ) Notice: Subject to any disclaimer, the term of this patent is extended or adjusted under 35 U.S.C. 154(b) by 320 days.

(21) Appl. No.: 14/168,020

(22) Filed: Jan. 30, 2014

(65) Prior Publication Data

US 2015/0045007 A1    Feb. 12, 2015

(51) Int. Cl.
| | | |
|---|---|---|
| *G06F 1/00* | (2006.01) | |
| *G06F 3/01* | (2006.01) | |
| *A61B 5/048* | (2006.01) | |
| *H04M 1/725* | (2006.01) | |
| *A61B 5/00* | (2006.01) | |

(52) U.S. Cl.
CPC .............. *G06F 3/015* (2013.01); *A61B 5/048* (2013.01); *H04M 1/7253* (2013.01); *A61B 5/6833* (2013.01); *H04M 2250/12* (2013.01); *H04M 2250/74* (2013.01)

(58) Field of Classification Search
CPC ..... G06F 3/167; G06F 17/30; G06F 17/30017
See application file for complete search history.

(56) References Cited

U.S. PATENT DOCUMENTS

| | | | | |
|---|---|---|---|---|
| 2008/0091090 A1* | 4/2008 | Guillory | .............. | A61B 5/0478 600/301 |
| 2012/0052905 A1* | 3/2012 | Lim | ........................ | G06F 3/015 455/550.1 |
| 2013/0338459 A1* | 12/2013 | Lynn | ................... | A61B 5/14552 600/323 |
| 2014/0040748 A1* | 2/2014 | Lemay | .................... | G06F 3/167 715/728 |
| 2014/0336473 A1* | 11/2014 | Greco | .................... | A61B 5/486 600/301 |
| 2015/0257674 A1* | 9/2015 | Jordan | ................. | A61B 5/0006 600/383 |
| 2015/0338917 A1* | 11/2015 | Steiner | .................. | H04L 9/3231 345/156 |

\* cited by examiner

*Primary Examiner* — Michael Faragalla

(57) ABSTRACT

Generally described, the present application relates to a system and method for processing input to control a set of functions and features. More specifically, however, the present application relates to user devices that can be controlled through brain activities or similar actions. In an illustrative embodiment, brain activities are monitored through electroencephalography (EEG). Through EEG, input waves that can be appropriately monitored can be sent to a virtual assistant. The virtual assistant can decipher the number of signals coming and determine a correct output such as a function or feature to be manipulated. In the implementation presented herein, features and functions of a smartphone can be manipulated. Other types of user devices can also be controlled, such as in-vehicle systems, head units, televisions, tablets, computer, laptops, etc.

1 Claim, 2 Drawing Sheets

Mind-Controlled Virtual Assistant on a Smartphone Device

Mind-Controlled Virtual Assistant on a Smartphone Device

Mind-Controlled Virtual Assistant on a Smartphone Device

MIND-CONTROLLED VIRTUAL ASSISTANT ON A SMARTPHONE DEVICE

This non-provisional application is a continuation-in-part of non-provisional application Ser. No. 14/168,020, entitled MIND-CONTROLLED VIRTUAL ASSISTANT ON A SMARTPHONE DEVICE, filed Jan. 30, 2014 by Duane Matthew Cash, and claims benefit under 35 USC 119(e) of provisional application 61/855,198, entitled MIND-CONTROLLED VIRTUAL ASSISTANT ON A SMARTPHONE DEVICE filed May 11, 2013 by Duane Matthew Cash.

TECHNICAL FIELD

This application generally relates to smartphones, and more particularly, to the control of functions and features within a smartphone through brain activities.

BACKGROUND

Today, smartphones have become the preferred choice of communications. From downloading content to making phone calls, these devices have become present in every aspect of our lives. A number of methods exist to provide input into the smartphone. For example, Blackberry devices have used a traditional keyboard and scroller. These devices, however, became obsolete as they failed to account for other types of input methods.

A giant share of the smartphone market is now dominated by Samsung and Apple who have quickly adapted the use of touchscreens into their devices. Users have become familiar with the different techniques of providing input through these touchscreens. In fact, over 25% of all new patent applications filed relate to some type of smartphone technology.

Soon, touchscreens however will become obsolete. The present application discloses a system and method of providing input into a smartphone, or other type of device through non-traditional activities.

SUMMARY

This summary is provided to introduce a selection of concepts in a simplified form that are further described below in the DESCRIPTION OF THE APPLICATION. This summary is not intended to identify key features of the claimed subject matter, nor is it intended to be used as an aid in determining the scope of the claimed subject matter.

In accordance with one aspect of the present application, a smartphone can have a virtual assistant that can be controlled by a human mind. The smartphone can communicate through a wireless or Bluetooth connection using a brainwave-analyzing device or headset worn by the user. The brainwave-analyzing device can be in the form of a headset with dry EEG sensors or a small wearable sensor patch worn on the forehead or throat of the user that contains the flexible EEG sensors, wireless communication oscillators, a wireless antenna and power coils.

A possible throat sensor patch can pick up sub-vocalizations in addition to the EEG patterns. The smartphone can run an application that analyzes the brainwave patterns sent from the EEG sensors and a thought recognition algorithm initiates the actions on the smartphone device. The user can receive feedback from the device in the form of speech synthesis as well as the target thought action. The system can be able to open menus, press buttons, play music and videos, use map navigation, make phone calls, and other smartphone-related activities that would previously be possible through a voice-activated virtual assistant. This system can use EEG wave patterns such as delta, theta, low alpha, high alpha, low beta, high beta, low gamma, and high gamma patterns to interact with the smartphone virtual assistant. The system can also accept manual operations from pressing an icon to activated voice-recognition algorithms.

BRIEF DESCRIPTION OF DRAWINGS

The novel features believed to be characteristic of the application are set forth in the appended claims. In the descriptions that follow, like parts are marked throughout the specification and drawings with the same numerals, respectively. The drawing figures are not necessarily drawn to scale and certain figures may be shown in exaggerated or generalized form in the interest of clarity and conciseness. The application itself, however, as well as a preferred mode of use, further objectives and advantages thereof, will be best understood by reference to the following detailed description of illustrative embodiments when read in conjunction with the accompanying drawings, wherein:

DETAILED DESCRIPTION OF DRAWINGS

Figure 1:
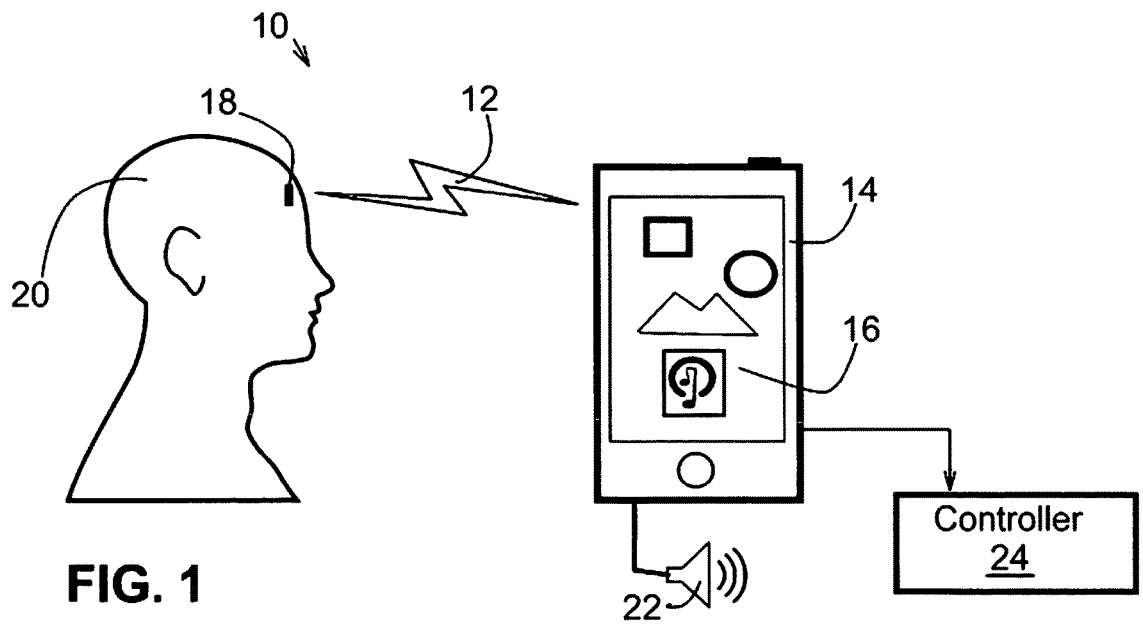
FIG. 1 is a diagram that shows illustrative components of a mind-controlled virtual assistant on a smartphone device in accordance with one aspect of the present application using an EEG sensor on the forehead.

FIG. 1 is a diagram that shows the components of a mind-controlled virtual assistant on a smartphone device 10 in accordance with one aspect of the present application that includes a dry EEG sensor or patch worn on the forehead 18, which detects the brainwave activity from the user 20. The EEG sensor and controller 18 sends the EEG signals to the smartphone device 14 via a wireless or Bluetooth signal 12 to a software application controller and method 24. The EEG patterns are processed and classified in the controller 24, and the intended user action is implemented on the smartphone device 14 where the visual action is presented on the user interface display 16 and any associated audio feedback such as text-to-speech for the intended user action is output with sound through the device speaker 22.

Figure 2:
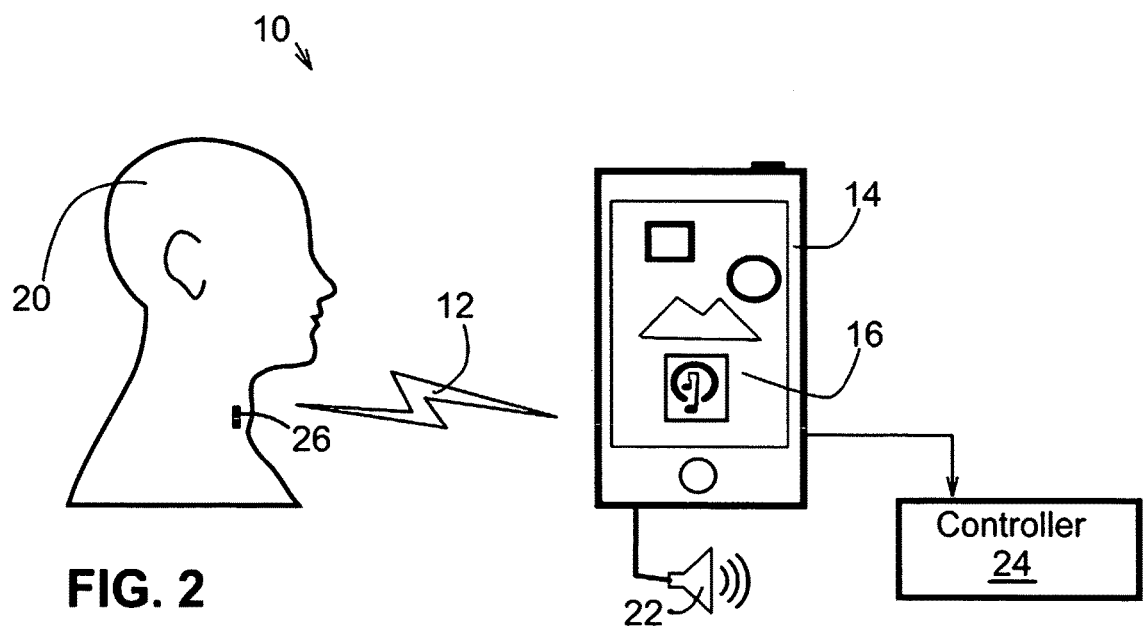
FIG. 2 depicts another embodiment similar to that of FIG. 1, except that the EEG sensor is placed on the throat to detect sub-vocalized brainwave patterns from the user.

FIG. 2 is a diagram that shows another embodiment of a mind-controlled virtual assistant on a smartphone device 10 in accordance with one aspect of the present application that includes a dry EEG sensor or patch worn on the throat 26, which detects the brainwave activity from the user 20. The EEG sensor and controller 26 sends the EEG signals to the smartphone device 14 via a wireless or Bluetooth signal 12 to a software application controller and method 24. The EEG patterns are processed and classified in the controller 24, and the intended user action is implemented on the smartphone device 14 where the visual action is presented on the user interface display 16 and any associated audio feedback such as text-to-speech for the intended user action is output with sound through the device speaker 22.

DESCRIPTION OF THE APPLICATION

The description set forth below in connection with the appended drawings is intended as a description of presently preferred embodiments of the application and is not intended to represent the only forms in which the present application may be constructed and/or utilized. The description sets forth the functions and the sequence of steps for constructing and operating the application in connection with the illustrated embodiments. It is to be understood, however, that the same or equivalent functions and sequences may be accomplished by different embodiments that are also intended to be encompassed within the spirit and scope of this application.

System Overview

Generally described, the present application relates to a system and method for processing input to control a set of functions and features. More specifically, however, the present application relates to user devices that can be controlled through brain activities or similar actions. In an illustrative embodiment, brain activities are monitored through electroencephalography (EEG). Through EEG, input waves that can be appropriately monitored can be sent to a virtual assistant. The virtual assistant can decipher the number of signals coming and determine a correct output such as a function or feature to be manipulated. In the implementation presented herein, features and functions of a smartphone can be manipulated. Other types of user devices can also be controlled, such as in-vehicle systems, head units, televisions, tablets, computer, laptops, etc.

The system and method described herein can provide a new way of presenting input that is more natural to the user. Furthermore, a user is no longer required to perform a lot of unnecessary input tasks as the system can define features and functions through brain activities. While this application is sought to be for smartphones, it does not necessarily have to be limited to such embodiments. For example, the described system and method can be used in tablets, personal computers, desktop computers, vehicle head units, and any other type of computing device. A number of advantages will become apparent from the description provided below.

Processing Brain Activities

A number of systems and methods can be used to detect brain activities of the user. Typically, brain activities are determined by measuring electrical activities along the scalp, otherwise known as Electroencephalography (EEG). EEG can measure voltage fluctuations resulting from ionic current flows within the neurons of the brain.

Devices that can measure the brain activities can come in a variety of forms. In conventional scalp EEG, the recording can be obtained by placing electrodes on the scalp with a conductive gel or paste, usually after preparing the scalp area by light abrasion to reduce impedance due to dead skin cells. Many systems typically use electrodes, each of which is attached to an individual wire. Some systems can use caps or nets into which electrodes are embedded; this is particularly common when high-density arrays of electrodes are needed.

Other Input Activities

Besides brain activities, the described system and method can use a number of other input methods. For example, voice can be used. Voice recognition and processing methods can be used to parse the language. The voice can be processed on board or off board. This in combination with determining brain activities can be used as a valuable tool to further process a number of inputs coming in from the user.

Other input activities can include detecting perspiration on the user. This can provide an indication that the user's stress level has increased. In combination with determining brain activities, this can be used in a number of applications, for example, driver distraction software run on vehicles. This type of software can reduce the driver distraction and focus the driver's priority on the road.

Gloves or similar devices can be used to track the user's activities as well. These types of devices can measure hand activities. The gloves/devices would be more directed towards measuring the nervousness of the user. Such applications exist in lie detector tests previously performed by law enforcement. Retinal scanning can also be used.

In one embodiment, the described system and method can include a patch or other attachment that can be placed around the user's vocal cords or throat. This type of device can detect a number of biometrics beyond that of voice. For example, this type of system can detect a user's intention to speak without the user actually speaking. This could open up an application that is more voice based.

It can be understood by the previous description that the described system and method can take in one or many inputs from the user. For example, the voice attachment can be used in combination with determining brain activities to alter a function or feature on the smartphone. Many more examples will be shown below, but do not limit this disclosure to such.

How It Works

Turning now to FIG. 1, the described system and method includes a smartphone virtual assistant that is controlled by the human mind. The system can include a smartphone that communicates via a wireless or Bluetooth connection with a brainwave-analyzing device or headset worn by the user. The brainwave-analyzing device can be in the form of a headset with dry EEG sensors or a small wearable sensor patch worn on the forehead or throat of the user that contains the flexible EEG sensors, wireless communication oscillators, a wireless antenna and power coils. A possible throat sensor patch would pick up sub-vocalizations in addition to the EEG patterns. The smartphone can run an application that analyzes the brainwave patterns sent from the EEG sensors and a thought recognition algorithm initiates the actions on the smartphone device. The user receives feedback from the device in the form of speech synthesis as well as the target thought action. The system can be able to open menus, press buttons, play music and videos, use map navigation, make phone calls, and other smartphone-related activities that would previously be possible through a voice-activated virtual assistant. This system would use EEG wave patterns such as delta, theta, low alpha, high alpha, low beta, high beta, low gamma, and high gamma patterns to interacted with the smartphone virtual assistant. The system will also be able to accept manual operation from pressing an icon to activated voice-recognition algorithms.

The MindGear system also can run in the background to allow mind-controlled operation with the smartphone in the pocket or purse of the individual. The controller contains algorithms that control voice and thought recognition, speech synthesis, feature activation, and artificial intelligence to allow for deeper integration levels with the virtual assistant. The system also contains algorithms for learning user behaviors and new words and concepts by performing web-mining techniques to catalog dictionary data and linguistic patterns.

The EEG headset monitors continuously for any data detected. Once data is detected, the raw EEG data readings are analyzed and an algorithm classifies them to the intended action. Below are some typical readings for some specific thought actions.

| | Smartphone Actions/EEG Headset Brainwave Patterns | | | | | | | |
|---|---|---|---|---|---|---|---|---|
| | Delta | Theta | High Alpha | Low Alpha | High Beta | Low Beta | High Gamma | Low Gamma |
| Open map | 296944 | 40920 | 11243 | 9738 | 17935 | 10607 | 2809 | 3004 |
| Close map | 20253 | 99901 | 18515 | 43749 | 8477 | 17100 | 786 | 3257 |
| Call | 23245 | 137119 | 114623 | 37692 | 13642 | 18538 | 1851 | 3925 |
| Exit phone | 4011 | 29849 | 11903 | 22140 | 6932 | 8353 | 1368 | 3170 |
| Play video | 570504 | 46768 | 16074 | 136170 | 9029 | 22683 | 2010 | 5412 |
| Open menu | 2989043 | 44610 | 2565 | 10697 | 9061 | 3801 | 1747 | 2758 |
| Close menu | 2234 | 27769 | 21516 | 29743 | 18374 | 13634 | 5400 | 4523 |
| Play music | 9730 | 27002 | 6513 | 53560 | 2887 | 14422 | 1522 | 2583 |
| Stop music | 106241 | 126436 | 20419 | 22041 | 16438 | 24646 | 3292 | 3936 |

Once the EEG data is classified, a processRecognition method is called to process the recognition phrase. The method will look for any recognition patterns that satisfy the condition and then trigger the action on the smartphone and provide text-to-speech feedback for the action. For the example of opening a map, once the method for receiving raw EEG data detects readings that fall within approximately 5 percent of the reading for delta, theta, high alpha, high beta, and high gamma, a variable is set with the contents of the "open map" and the controller executes the process Recognition method. The processRecognition method will compare the recognition phrase against a list of commands and look for a match. Once a match is found, the view index will change to the intended action view (i.e., a view containing the map) and an algorithm will activate speech synthesis to say "Opening the map now" or some other verbal feedback to inform the user of the successful action. A speech bubble is also displayed that contains the recognized phrase and smartphone response.

After successful processing of the brainwave activity, the system will delay a number of seconds before the raw brainwave activity is monitored again in order to prevent multiple triggers of the same command.

Implementation

The technology described herein can be implemented as logical operations and/or modules. The logical operations can be implemented as a sequence of processor-implemented steps executing in one or more computer systems and as interconnected machine or circuit modules within one or more computer systems. Likewise, the descriptions of various component modules can be provided in terms of operations executed or effected by the modules. The resulting implementation is a matter of choice, dependent on the performance requirements of the underlying environment in which the described disclosure is implemented. The logical operations making up the embodiment of the disclosure described herein are referred to variously as operations, steps, objects, or modules. It should be understood that logical operations can be performed in any order, unless explicitly claimed otherwise or a specific order is inherently necessitated by the claim language.

Various embodiments of the present disclosure can be programmed using an object-oriented programming language, such as SmallTalk, Java, C++, Ada, or C#. Other object-oriented programming languages can also be used. Alternatively, functional, scripting, and/or logical programming languages can be used. Various aspects of this disclosure can be implemented in a non-programmed environment, for example, documents created in HTML, XML, or other format that, when viewed in a window of a browser program, render aspects of a GUI or perform other functions. Various aspects of the disclosure can be implemented as programmed or non-programmed elements, or any combination thereof.

In software implementations, computer software and/or data is stored on a machine readable medium as part of a computer program product, and is loaded into a computer system or other device or machine via a removable storage drive, hard drive, or communications interface. Computer programs, also called computer control logic or computer readable program code, are stored in a main and/or secondary memory, and executed by one or more processors, controllers, or the like to cause the one or more processors to perform the functions of the disclosure as described herein.

The figures and examples above are not meant to limit the scope of the present disclosure to a single embodiment, as other embodiments are possible by way of interchange of some or all of the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present disclosure, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description is provided to enable any person skilled in the relevant art to practice the various embodiments described herein. Various modifications to these embodiments will be readily apparent to those skilled in the relevant art, and generic principles defined herein may be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. A system for a mind-controlled virtual assistant on a smartphone device, comprising:
   at least one wearable electroencephalography (EEG) sensor worn on the forehead or throat of the user, the at least one EEG sensor comprising one or more electrodes, and configured to detect EEG brainwave patterns;
   a controller configured to send the EEG brainwave patterns to a smartphone device via a wireless protocol;
   the smartphone device comprising:
      a machine-readable medium having a computer algorithm stored thereon for executing the steps of:
      receiving a user input of the detected EEG brainwave patterns in the form of raw EEG brainwave signals via a wireless protocol,
      classifying the received raw EEG brainwave signals by mapping different smartphone actions to different EEG brain patterns,
      when the algorithm detects that a received brainwave pattern satisfies a mapped smartphone action, the algorithm triggers the mapped smartphone action,
      providing text to speech feedback for the triggered mapped action,
      preventing multiple triggers of the executed mapped action by delaying a monitoring of the raw EEG brainwave signals after successful processing of the triggered mapped action.

* * * * *